United States Patent [19]

Nishigaki

[11] Patent Number: 5,051,824
[45] Date of Patent: Sep. 24, 1991

[54] ELECTRONIC SCOPE HAVING DETACHABLE FRAME TO WHICH SOLID STATE IMAGING DEVICE IS FASTENED

[75] Inventor: Shinichi Nishigaki, Tokyo, Japan

[73] Assignee: Olympus Optical Co., Ltd., Tokyo, Japan

[21] Appl. No.: 593,913

[22] Filed: Oct. 5, 1990

[30] Foreign Application Priority Data

Oct. 30, 1989 [JP] Japan .................................. 1-283496
Jul. 30, 1990 [JP] Japan .................................. 2-204887

[51] Int. Cl.[5] ......................... H04N 1/04; H04N 1/06
[52] U.S. Cl. ......................................... 358/98; 128/6
[58] Field of Search ............................... 358/98; 128/6

[56] References Cited

U.S. PATENT DOCUMENTS

| | | | |
|---|---|---|---|
| 3,499,107 | 3/1970 | Sheldon | 358/98 |
| 4,491,865 | 1/1985 | Danna et al. | 358/98 |
| 4,697,210 | 9/1987 | Toyota et al. | 358/98 |
| 4,867,138 | 9/1989 | Kubota et al. | 128/6 |

FOREIGN PATENT DOCUMENTS 63-259613 10/1988 Japan .
63-286125 11/1988 Japan .

Primary Examiner—Howard W. Britton
Attorney, Agent, or Firm—Armstrong, Nikaido, Marmelstein, Kubovcik, & Murray

[57] ABSTRACT

An electronic scope arranged in such a manner that an objective lens system is fastened to the tail end portion of an elongated inserting section and a solid state imaging device having a photoelectric transfer function is disposed at the focal point of the objective lens system. A frame to which the solid state imaging device is fastened to the tail end portion thereof is arranged to be detachably fastened to the inserting section. Therefore, the solid state imaging device can be easily repaired or interchanged by draawing out the frame body from the inserting section.

25 Claims, 7 Drawing Sheets

ELECTRONIC SCOPE HAVING DETACHABLE FRAME TO WHICH SOLID STATE IMAGING DEVICE IS FASTENED

BACKGROUND OF THE INVENTION

1. Field of the Invention

The present invention relates to an electronic scope arranged in such a manner that a frame body, to which a solid state imaging device is fastened, is detachably inserted into an inserting section so that the solid state imaging device can be easily interchanged.

2. Description of the Related Art

Recently, an electronic scope has been widely used which is capable of forming an image of a portion of the body cavity of a patient to be observed by using imaging means which employs a solid state imaging device such as a charge coupled device (CCD) by inserting an elongated portion of the electronic scope into a portion of the body cavity to be observed (to be called a "observation portion" hereinafter).

An electronic scope of the type described above has an advantage in that an excellent resolution can be obtained in comparison to the fiber scope and another advantage in that image processing such as an enlargement of an image and a comparison of two images can be easily performed. There are two types of methods of forming a color image in the above-described electronic scope, that is, a plane successive method in which illuminating light is successively switched to red, green and blue and a color mosaic method (also called a "simultaneous method") in which color filters through which respective color light beams red, green and blue can pass through are placed in front of the solid state imaging device, the color filters being placed in a mosaic manner. The plane successive method has an advantage with respect to the color mosaic method in that the number of pixels can be reduced, while the color mosaic method has an advantage in that an off color can be prevented.

As disclosed in Japanese Patent Laid-Open No. 63-259613 and Japanese Patent Laid-Open 63-286125, the above-described solid state imaging device has been adhered to an inner tube which constitutes the inserting section.

According to the above-described conventional structures, the solid state imaging device, which can be most easily broken, is secured to the forward elements or the inner tube which constitutes the inserting section. Therefore, if the solid state imaging device is desired to be interchanged for the purpose of subjecting it to a repairing operation or the like, the above-described elements which constitute the inserting section must be respectively disassembled.

However, the above-described elements constituting the inserting section are strongly secured and hermetically sealed up for the purpose of preventing their separation when the inserting section is inserted into the body cavity and maintaining the water tightness. Therefore, the elements constituting the inserting section cannot be easily assembled/disassembled. As a result, a too long time undesirably takes to complete the assembling/disassembling work, causing a trouble in the inspection and curing schedule in the hospital. Furthermore, the disassembled elements may not be completely assembled again, causing the separation of the elements or water leakage to occur. As described above, it has been difficult to maintain the quality of the electronic scope after it has been subjected to the repairing operation.

SUMMARY OF THE INVENTION

Accordingly, an object of the present invention is to provide an electronic scope arranged in such a manner that its solid state imaging device can be easily repaired/interchanged without a necessity of respectively disassembling the elements of the inserting section thereof.

Another object of the present invention is to provide an electronic scope capable of preventing the deterioration in the quality and the durability even if the solid state imaging device is repaired/interchanged.

An aspect of the present invention lies in an electronic scope comprising: an elongated inserting section; a main body section to which the end portion of the inserting section is fastened; an objective lens system fastened to the front portion of the inserting section and arranged to form an optical image; a light guide allowed to pass through the inserting section and arranged to transmit illuminating light so as to emit it through the end portion thereof; a frame body the base portion of which is fastened to the main body section and the tail end portion of which is inserted into the inserting section until it reaches a position in the vicinity of the focal position of the objective lens; a solid state imaging device fastened to the tail end portion of the frame body, the solid state imaging device having a photoelectric transfer function; and securing means for detachably securing at least either the inserting section except for the frame body or the base portion of the frame body to the main body section. Since the frame body can be arranged to be detachable with respect to the inserting section by the securing means, the solid state imaging device can be easily interchanged/repaired by drawing out the frame body from the inserting section.

Other and further objects, features and advantages of the invention will be appear more fully from the following description.

BRIEF DESCRIPTION OF THE DRAWINGS

FIG. 1 is a cross sectional view which illustrates an electronic scope;

FIG. 2 illustrates the overall structure of an electronic scope system;

FIG. 3 is a cross sectional view which illustrates a frame tube portion from which the outer tube is removed and to which a solid state imaging device is fastened;

DESCRIPTION OF THE PREFERRED EMBODIMENTS

Figure 2:
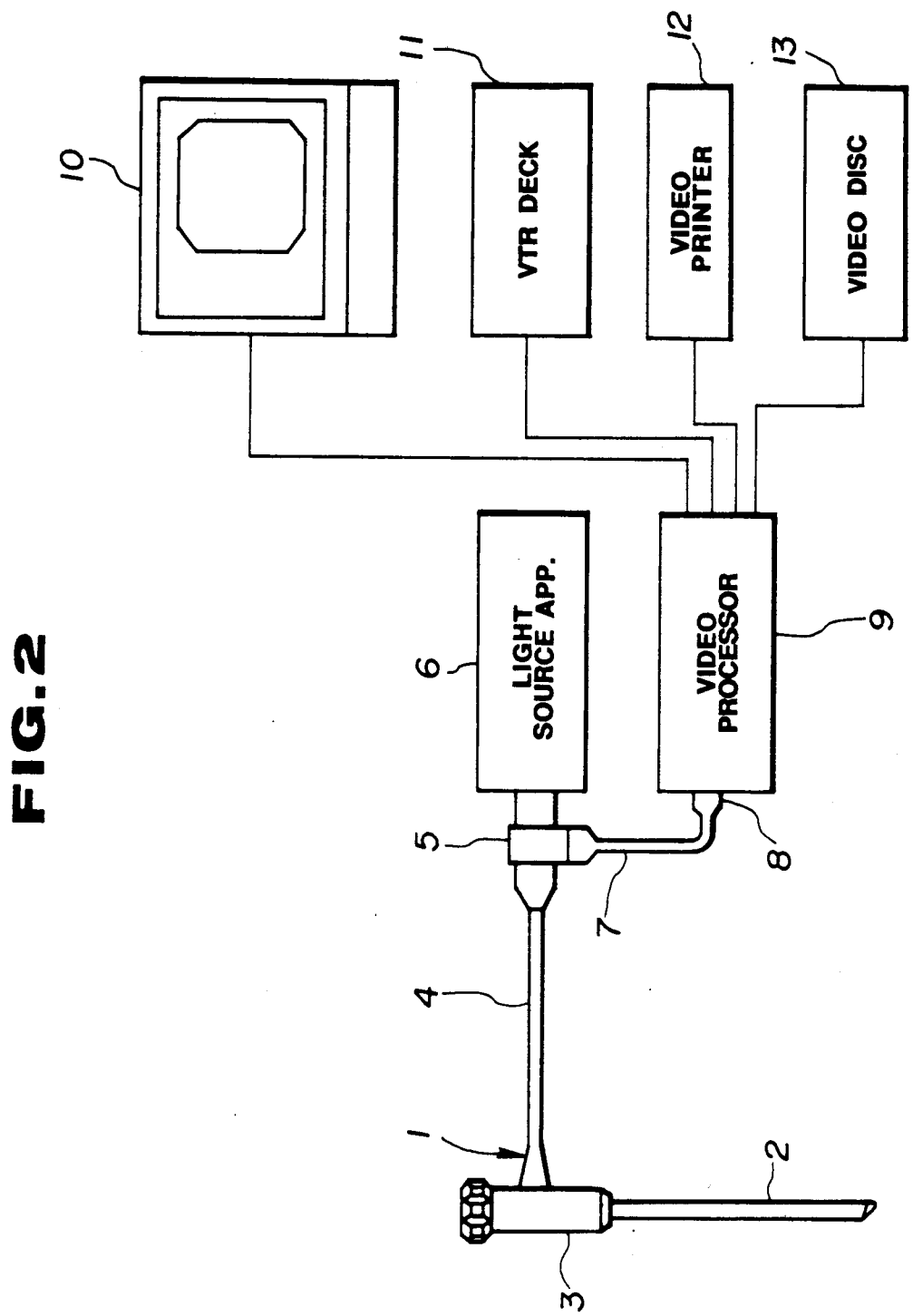

As shown in FIG. 2, an electronic sccpe system comprises an electronic scope 1 according to a first embodiment of the present invention, a light source apparatus 6 for supplying illuminating light to the electronic scope 1, a video processor 9 for processing a signal transmitted from imaging means of the electronic scope 1, a monitor 10 for displaying the image of a subject in response to an image signal transmitted from the video processor 9, a VTR deck 11 for recording the image signal, a video disk 13 and a video printer 12 for printing the image of the subject.

The electronic scope 1 comprises an elongated and hard inserting section 2 and a main body section 3 connected to the rear end portion of the inserting section 2, the main body section 3 having a relatively larger diameter. The main body section 3 has a flexible universal cord 4 extending from the side portion thereof, the universal cord 4 having a connector 5 in the end portion (the terminus) thereof. The connector 5 can be detachably connected to the light source apparatus 6 so that illuminating light is supplied from the light source apparatus 6.

A signal cord 7 extends from the connector 5, the signal cord 7 having a signal connector 8 in the end portion thereof. The signal connector 8 can be connected to the video processor 9. The above-described monitor 10, the VTR deck 11, the video printer 12, the video disk 13 and the like can be connected to the video processor 9.

Figure 1:
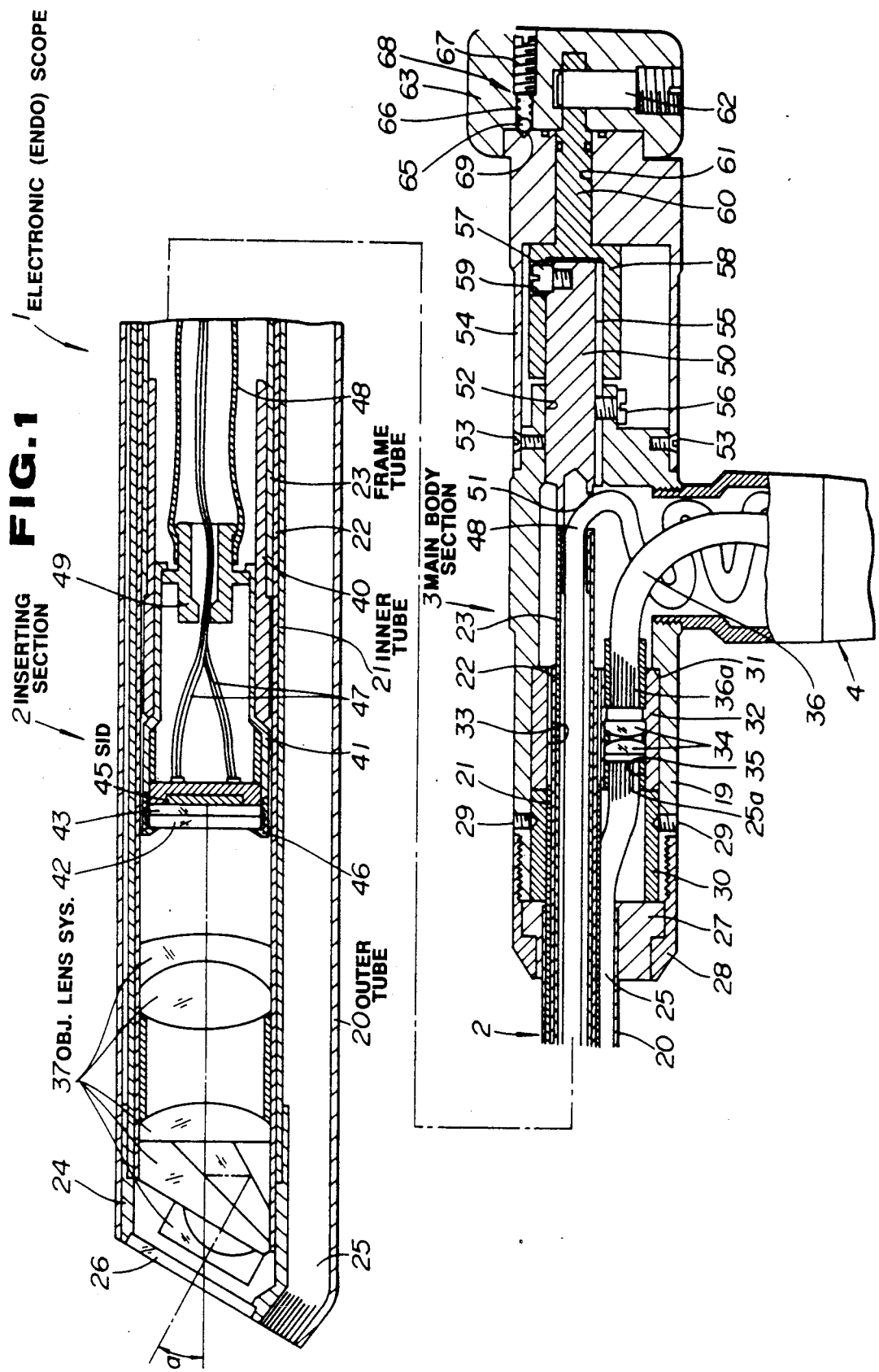
FIGS. 1 to 3 respectively illustrate a first embodiment of the present invention, where

As shown in FIG. 1, the inserting section 2 is in the form of a hard quadruplex pipe (tube) comprising an outer tube 20, an inner tube 21 eccentrically disposed with respect to the outer tube 20, a lens tube 22 disposed inner than the inner tube 21 and a frame tube 23 disposed inner than the lens tube 22 (FIG. 1 illustrates the enlarged state of the cross sectional shape of the front portion of the inserting section 2).

The inner tube 21, having a cover glass frame 24 secured to the front portion (the terminus) thereof, is inserted into the outer tube 20. The gap formed between the inner wall of the outer tube 20 and the outer wall of the inner tube 21 is filled with a light guide bundle 25 which acts to introduce illuminating light supplied from the light source apparatus 6, the light guide bundle 25 being adhered and secured to that position.

A cover glass 26 is disposed is the front portion of the cover glass frame 24 in such a manner that it forms one plane in cooperation with the end surface of the outer tube 20 and that of the light guide bundle 25. According to this embodiment, the front portion of the outer tube 20 has an end portion (adjacent to the bottom portion) bent toward the other end portion by a certain degree. Furthermore, the end surface of the outer tube 20 is arranged to be slanted in such a manner that the portion adjacent to the bottom portion projects over the other portion.

A flange 27 is disposed in the end portion (the base portion), which is adjacent to the operator, of the outer tube 20, the flange 27 being detachably fastened to the end surface of the main body section 19 in such a manner that a nut 28 is screwed by a male screw portion formed on the outer surface of the front portion of a main body 19 which forms the main body section 3.

The end portion, which is adjacent to the operator, of the inner tube 21 is arranged to project into the main body 19 from the flange 27 of the outer tube 20 until it reaches the portion in the vicinity of the front surface of a light distributing lens frame 32. That is, the end portion, which is adjacent to the operator, of the inner tube 21 extends to the portion in the vicinity of the front surface of the light distributing lens frame 32 which is positioned in contact with a step portion 31 formed in the main body 19 by a ring 30 secured to a portion in the main body 19 by a screw 29.

The light distributing lens frame 32 has a through hole 33 the inner diameter of which is slightly larger than the outer diameter of the inner tube 21, the through hole 33 being formed coaxially with the inner tube 21. Furthermore, a through hole, that is, a light guide hole 35 which accommodates the light distributing lens 34 is formed below the through hole 33. An end portion 25a, which is adjacent to the operator, of the light guide bundle 25 is disposed in the forward portion of the light guide hole 35. Furthermore, an end portion 36a of a light guide bundle 36 another end of which is accommodated in the universal cord 4 and which is fixed to a portion within the connector 5 is disposed in the portion of the light guide hole 35, the light guide bundle 36 acting to transmit light supplied from the light source apparatus. The above-described end portions 25a and 36a are disposed in such a manner that the light distributing lens 34 is interposed between them and light emitted from the end portion 36a of the light guide bundle 36 is made incident upon the end portion 25a, which is adjacent to the operator, at a wide light distribution angle. The end portions 25a and 36a of the respective light guide bundles 25 and 36 are detachably secured to the light distributing lens frame 32 by screws (omitted from illustration).

The lens tube 22 is inserted into the inner tube 21 and an objective lens system 37 is accommodated and adhered to the inner front portion of the lens tube 22. A first lens, which is a component of the objective lens system 37 and disposed adjacent to the front portion (light incidental side) of the lens tube 22, is positioned adjacently so as to confront the cover glass 26 in the front portion of the inner tube 21. A tail end (light emitting side) lens is fastened so as to confront the photoelectric transfer surface of the solid state imaging device 45. The first lens is fastened in such a manner thin the optical axis thereof makes a certain angle a (however, smaller than 90 degrees) with the axis of the inserting section 2. The direction of the optical axis of the first lens is arranged to be the direction of the visual field of the electronic scope 1 according to the present invention. Thus, light, made incident along the above-described direction, further travels along the optical axis of the tail end lens. As a result, the light is imaged on the photoelectric transfer surface of the solid state imaging device 45 disposed in such a manner thin its central portion is disposed on the above-described axis. Thin is, the electronic scope 1 is a perspective visual type the visual field of which is arranged to be in the diagonally forward direction.

The end portion, which is adjacent to the operator, of the lens tube 22 further extends into the through hole 33 formed in the light distributing lens frame 32 over the inner tube 21 which projects into the main body 19. As a result, when the lens tube 22 is inserted into the inner tube 21, the position of the objective lens system 37 with respect to the position of the cover glass 26 can be easily adjusted because the end portion, which is adjacent to the operator, of the lens tube 22 and which projects over the inner tube 21 can be held by the hand. After the above-described positioning has been completed, the end portion, which is adjacent to the operator, of the inner tube 21 and the lens 22 are adhered to each other.

A frame tube 23 to which a device frame 41 is secured in the front portion thereof via a front frame 40 is movably inserted into the portion, which is adjacent to the operator, of the objective lens system 37 which is disposed in the above-described lens tube 22, the frame tube 23 serving as a frame member. A infrared ray cutting filter 42, a quartz filter 43 and a mosaic filter (omitted from illustration) are pasted to the front portion of the device frame 41, if necessary. Furthermore, the solid state imaging device 45 having the photoelectric transfer function is secured by a nut 46 in the above-described front portion of the device frame 41. In addition, a signal line 47 extending from the rear side (reverse side) of the solid state imaging device 45 and a cord retainer 49 for securing a shielding member 48 for protecting the overall length of the signal line 47 in the region from the frame tube 23 to the connector 5 are disposed there. The rear end portion of the device frame 41 is inserted and fixed to the front portion of the front frame 40 and the rear end portion of the front frame 40 is inserted and fixed to the front portion of the frame tube 23. The signal line 47 covered by the shielding member 48 is introduced into the main body 19 through the frame tube 23. The signal line 47 is further introduced into the universal cord 4 so as to be connected to the connector 5, the signal line 47 being introduced through a cut 51 formed in a slide shaft 50 connected to the end portion of the frame tube 23 which projects into the main body 19 over the end portion, which is adjacent to the operator, of the lens tube 2 accommodated in the main body 19.

A slide shaft retainer 52 is formed (in the form of a hole) in the end portion, which is adjacent to the operator, of the main body 19. Thus, the rear end portion of the above-described slide shaft 50 projects in a cam shaft retainer 54 which is disposed next to the slide shaft retainer 52 in the portion, which is adjacent to the operator, of the main body 19 by a screw 53. Furthermore, the rear end portion of the slide shaft 50 is held by a slide pin 56 so as to be movable in its axial direction, the slide pin 56 projecting from the slide shaft retainer 52 into a key groove 55 formed in the outer surface of the slide shaft 50. A cam pin 57 projects from the rear end portion of the slide shaft 50 which projects in the cam shaft retainer 54. The cam pin 57 is formed so as to project into a cam grove 59 formed in the outer surface of a cam ring 58 disposed so as to be connected to the rear end portion of the slide shaft 50 in such a manner that a certain angle is made with respect to the axial direction.

A cam shaft 60 is formed in the portion, which is adjacent to the operator, of the cam ring 58, the cam shaft 60 projecting over a through hole 61 formed in the rear end portion of the cam shaft retainer 54 toward the operator. The cam shaft 60 is secured to a knob 63 which is, by a screw 62, rotatably fastened to the rear end surface of the cam shaft retainer 54. That is, when the knob 63 is rotated, the cam ring 58 is rotated so that the rotational force is transmitted to the slide shaft 50 via the cam groove 59 and the cam pin 57. As a result, the slide shaft 50 moves in the axial direction by the restriction action performed by the slide pin 56. Therefore, also the frame tube 23 connected to the slide shaft 50 is axially moved. As a result, the distance between the solid state imaging device 45 disposed in the front portion of the frame tube 23 and the objective lens system 37 can be adjusted. Consequently, the focus adjustment operation can be performed.

A click groove 69 is formed in the end surface, which is adjacent to the operator, of the cam shaft retainer 54 at a position corresponding to a click mechanism formed in the knob 63 and constituted by a ball 65, a spring 66 and a screw 67. As a result, the established focus adjusted position can be maintained.

Then, the operation of this embodiment will be described.

A description will be made about a case in which a failed solid state imaging device 45 is interchanged.

All of the outer tube 20 and the flange 27, the light guide bundle 25, the inner tube 21 successively disposed in the portion which is adjacent to the operator, the cover glass frame 24 disposed in the front portion and sealed by the cover glass 26 and the lens tube 22 for accommodating the objective lens system 37 are integrally formed with the inserting section 2 by an adhesive or the like. Although the solid state imaging device 45 is secured to the front portion of the frame tube 23, it is able to move with respect to the position of the inserting section 2 (with respect to the lens tube 22 of the inserting section 2), the solid state imaging device 45 being fastened within the main body section 3. Furthermore, the inserting section 2 is simply secured to the main body section 3 due to a fact that the flange 27 is detachably fastened to the main body 19 by the nut 28 and a fact that the end portion 25a of the light guide bundle 25 is also detachably fastened to the light distributing lens frame 32 by a screw (omitted from illustration). Therefore, in the case where the solid state imaging device 45 in interchanged, the nut 28 is first removed from the main body 19.

Then, the screw (omitted from illustration), which is securing the end portion 25a of the light guide bundle 25, is removed. As a result, the inserting section 2 and the main body 19 are brought to disconnected state.

Figure 3:
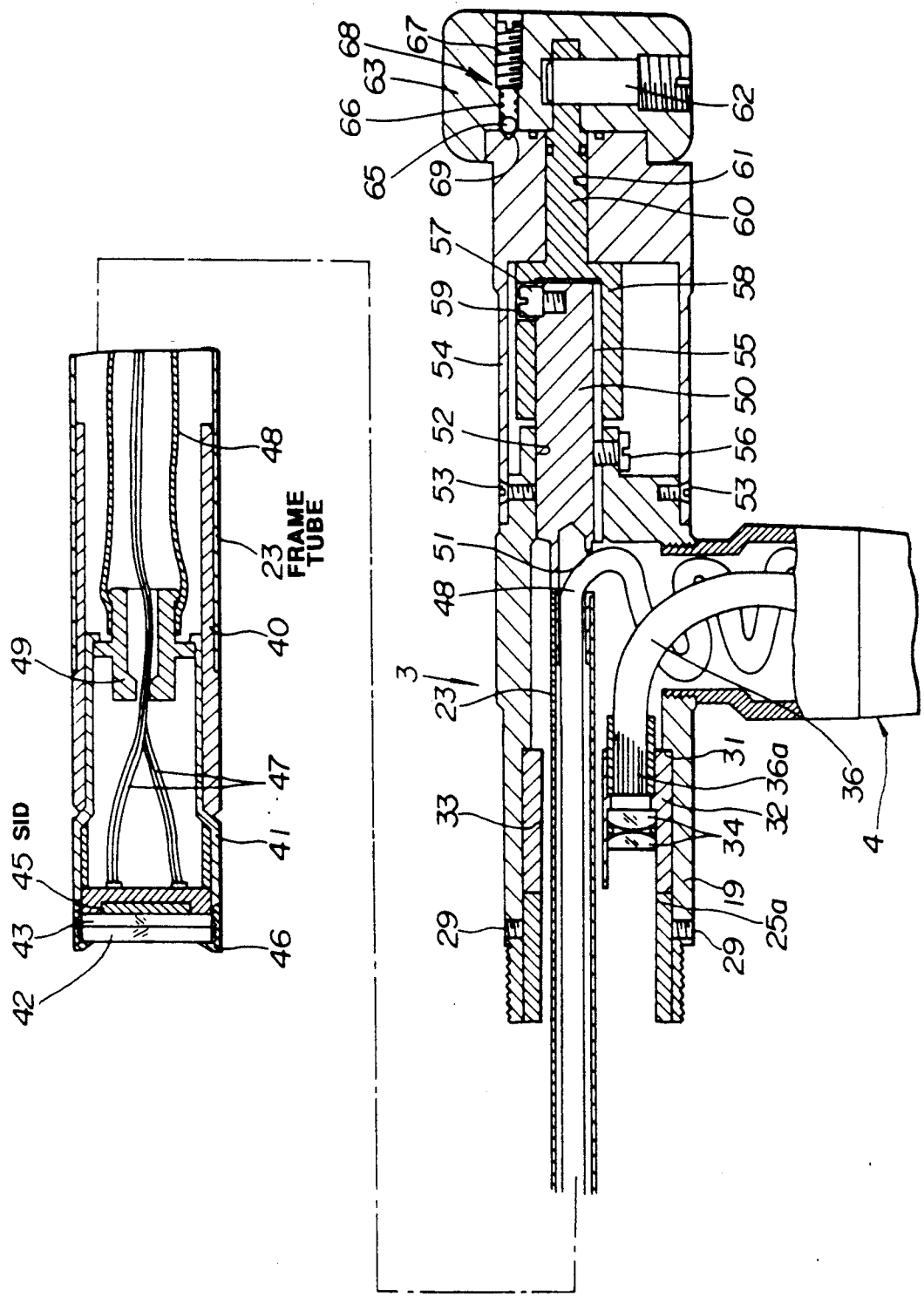

When the inserting section 2 is then drawn from the main body 19 toward the front portion, the inserting section 2 can be removed from the main body section 3 with the solid state imaging device 45 left in the main body section 3 without a necessity of disassembling the elements of the inserting section 2. That is, when the inserting section 2 is forwardly drawn out from the main body 19, the portion including the frame tube 23 to which the solid imaging device 45 is fastened can be separated from the portion including the lens tube 22 to which the inner tube 21 and the objective lens system 37 are secured. As a result, the portion including the frame tube 23 becomes as shown in FIG. 3.

After the inserting section 2 has been drawn out from the main body 19, the device frame 41 to which the solid state imaging device 45 is fastened by the nut 46 appears outside (at the front portion of the frame tube). Therefore, the solid state imaging device 45 can be easily repaired or interchanged after the nut 46 has been removed.

The assembling of the above-described elements to be performed after the solid state imaging device 45 has been interchanged or repaired must be performed conversely to the elements removal order. At this time, when the objective lens system 37 and the solid state imaging device 45 are relatively positioned to each other, the knob 63 must be rotated after assembling the inserting section 2 and the main body section 3 in a predetermined manner. As a result, the fine positional adjustment of the solid state imaging device 45 in the direction of the optical axis of the objective lens system 37 can be performed. Therefore, the focus adjustment can be performed.

According to this embodiment, the solid state imaging device 45 can be easily removed by drawing the frame tube 23 from the inserting section 2 with eliminating a necessity of disassembling the elements of the inserting section 2. Therefore, the time taken for completing the repairing or the like can be shortened. As a result, the operation yield can be improved in the inspection and curing operation in the hospital.

Furthermore, since the elements constituting the outer shell of the front portion (terminal end) of the inserting section 2 are not disassembled at the time of the repairing operation, the separation of the elements constituting the outer shell and water leakage from the same can be prevented. As a result, a high quality and durability can be maintained even if the repairing operation is performed.

Figure 4:
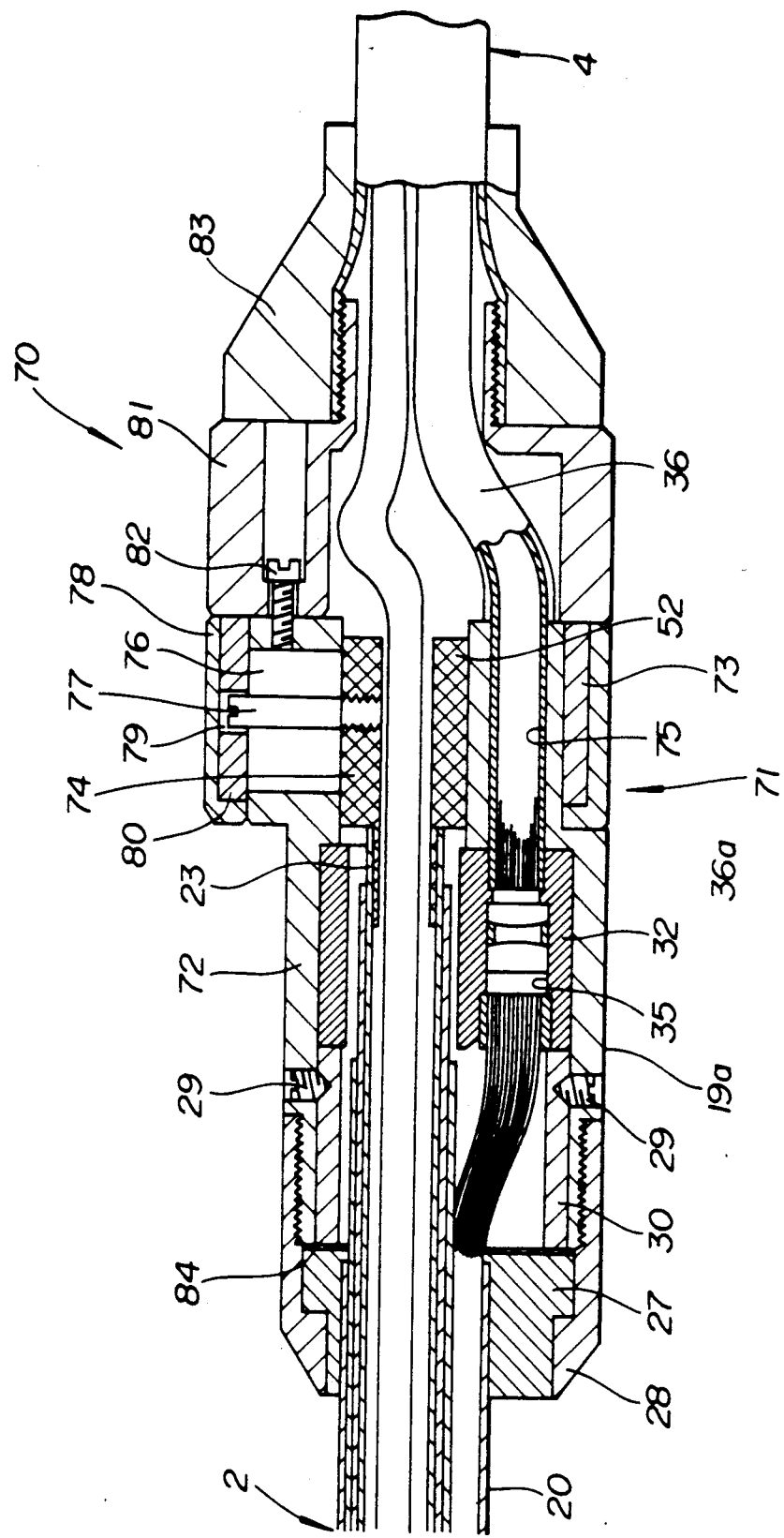
FIG. 4 is a cross sectional view which illustrates a main body section according to a second embodiment of the present invention.

FIG. 4 is a cross sectional view which illustrates a main body section 71 of an electronic scope 70 according to a second embodiment.

Although the universal cord 4 is, in the main body section, allowed to extend perpendicularly to the axial direction of the inserting section 2 according to the first embodiment, the universal cord 4 is allowed to backwards extended from the end surface, which is adjacent to the operator, of the main body section 71. The front portion of the inserting section 2 is the same as that according to the first embodiment and the front portion of the main body section 71 is substantially the same as the corresponding portion according to the first embodiment.

Similarly to the first embodiment, the flange portion 27 of the inserting section 2 is, via the nut 28, detachably secured to the front portion of the main body 72 constituting the main body section 71. However, according to this embodiment, a rubber ring 84 serving as a hermetically sealing member is fastened to the end surface, which is adjacent to the operator, of the flange portion 27 so that the inside portion is hermetically protected from water. The rubber ring 84 may be fastened to the front surface of the main body 72 (the rubber ring 84 may as well be applied to the first embodiment).

An outer surface 73, which is adjacent to the operator, of the main body 72 is eccentrically disposed with respect to an outer surface 19a of the forward portion of the main body 72. The outer surface 73 is disposed coaxially with a bearing 52 for rotatably supporting the slide shaft 74 disposed in the end portion, which is adjacent to the operator, of the frame tube 23.

The end portion 36a of the light guide bundle 36 is secured in a through hole 75 disposed below the bearing 52 in such a manner that the end portion 36a projects from the portion which is adjacent to the operator into the light guide hole 36 of the light distributing lens frame 32. A slide groove 76 connected to the outer surface 73, which is adjacent to the operator, of the main body 72 is formed above the bearing 52 so that a cam pin 77 projecting over the outer surface from the slide shaft 73 is made to be moveable in the axial direction (of the inserting section 2).

A cam ring 80, to which a focusing ring 78 having a knurled surface on the outer surface thereof is fitted around the outer surface thereof and having a cam groove 79 into which the front portion (the top end) of the cam pin 77 can be inserted, is rotatably fitted around the outer surface 73 of the main body 72. Therefore, when the focusing ring 78 is rotated, the cam pin 77 is moved in the cam groove 79 and the slide groove 76. As a result, the slide shaft 4 can be moved in its axial direction.

A cap 81 is secured to the end surface, which is adjacent to the operator, of the main body 72 by a screw 82. The universal cord 4 passing through the cap 81 is secured in the rear end portion, which is adjacent to the operator, of the cap 81 by a holder 83. The axial undesirable movement of the cam ring 80 can be prevented by fixing the cap 81 by the screw 82.

The other structures are the same as those according to the first embodiment.

As a result of the structure thus constituted, the universal cord 4, the inserting section 2 and the main body section 71 can be aligned. Therefore, an effect can be obtained in that the universal cord 4 does not come in contact with the body wall of a patient even if the body wall is penetrated by the scope 70, which can be easily handled, with inclined to a degree substantially in parallel to the body wall of the patient. Furthermore, even after the solid state imaging device 45 has been repaired, a hermetically sealed state can be realized in which water invasion into the joint portion between the rear end portion, which is adjacent to the operator, of the outer tube 20 and the front portion of the main body 72 is prevented by tightening the nut 28 so as to cause the rubber ring 84 to be pressed by the rear end surface, which is adjacent to the operator, of he flange portion 27 and the front surface of the main body 72. Therefore, the deterioration in the characteristics of the solid state imaging device 45 due to water or its failure can be satisfactorily prevented. The other operations and effects are the same as those according to the first embodiment.

Figure 5:
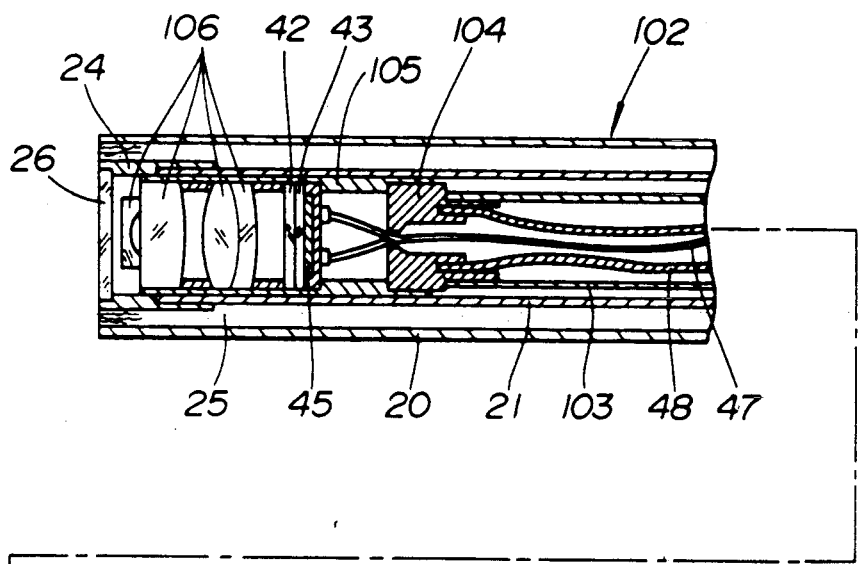
FIG. 5 is a cross sectional view which illustrates the electronic scope according to a third embodiment of the present invention.
Figure 5:
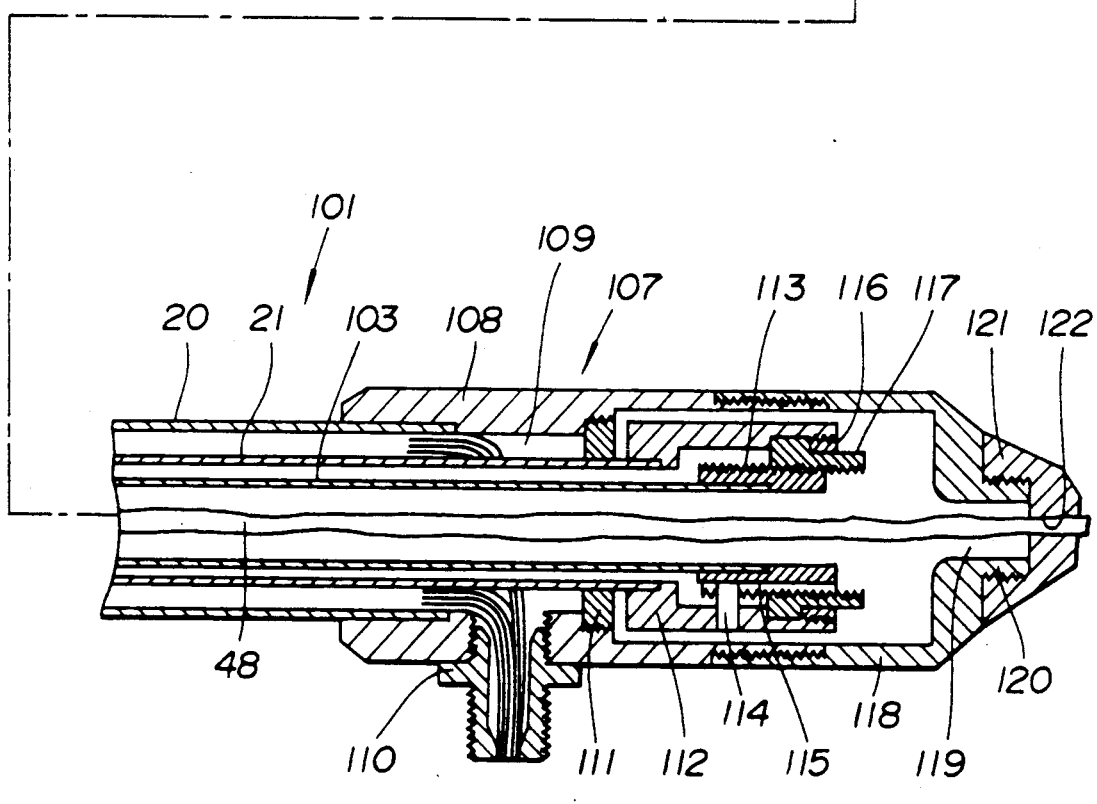

FIG. 5 is a cross sectional view which illustrates a third embodiment of an electronic scope 101.

As shown in FIG. 5, according to this embodiment, the inner tube 21 is coaxially (concentrically) inserted into the outer tube 20 which forms an inserting section 102. The light guide bundle 25 is disposed between the outer tube 20 and the inner tube 21. A frame tube 103 serving as a direct frame member is movably inserted into the inner tube 21. Therefore, also the frame tube 103 is inserted concentrically with the inserting section 102.

A device frame 105 is disposed in the front portion of the frame tube 103 via a cord retaining member 104. The device frame 105 accommodates, when viewed from the front portion, an objective lens system 106, the infrared ray cutting filter 42, the quartz filter 43, the mosaic filter and the solid state imaging device 45 in this sequential order.

According to this embodiment, the optical axis of the objective lens system 106 is made coincide with the central axis of the frame tube 103. Therefore, the above-described objective lens system 106 constitutes a direct-view type objective lens system arranged in such a manner that the direction of the visual field is made to be the axial direction of the inserting section 102.

The end portion of the above-described outer tube 20 is directly connected to a main body 108 of the main body section 107. Furthermore, the light guide bundle 25 disposed between the outer tube 20 and the inner tube 21 passes through a space 109 in the main body 108 until it reaches a joint 110 which is allowed to project on the side wall of the main body 108.

According to the third embodiment, the light source apparatus 6 and the joint 110 are directly connected to each other by a light guide cord (omitted from illustration). Therefore, illuminating light is introduced into the front portion of the inserting section 102.

The end portion, which is adjacent to the operator, of the inner tube 21 is allowed to project in the space 109 in the main body 108 over the joint 110. The inner tube 21 is held by a nut 111 which seals the space 109 from the portion adjacent to the operator, the inner tube 21 further extending over the nut 11 until it reaches a retaining member 111 to which it is connected. A screw 113 connected to the end portion, which is adjacent to the operator, of the frame tube 103 is disposed in the retaining member 112, the frame tube 103 being allowed to extend through the inner tube 21. The screw 113 has a key groove 115 formed in the axial direction and on the outer surface thereof to which a slide pin 114, allowed to project from the side wall of the retaining member 112 toward inside, projects. Furthermore, the screw 113 is screwed and held by a rotary screw 117 rotatably fastened by a nut 116 in the end portion, which is adjacent to the operator, of the retaining member 112.

The end portion, which is adjacent to the operator, of the main body 108 is screwed with a cover 118 formed so as to cover the retaining member 112. A cable hole 119 is allowed to pass through the central portion of the end portion, which is adjacent to the operator, of the cover 118, the cable hole 119 being connected to a hole 122 of a holder 121 screwed with a holder 120 formed on the outer surface, which is adjacent to the operator, of the cover 118. The signal line 47 and the shield 48 extending through the frame tube 103 passes through the above-described holes 121 and 122 so as to be connected to the connector 5.

The other structures are the same as those according to the first embodiment.

Then, the operation of this embodiment will be described.

In the case where the solid state imaging device 45 is interchanged, the cover 118 screwed to the portion, which is adjacent to the operator, of the main body 108 is removed before the rotary screw 117 is rotated, for example, clockwise (in the case where the screw 113 and the rotary screw 117 are right-handed screws). As a result, the screw 113 is not rotated and retracted by the action of the slide pin 114, causing the overall body of the screw 113 to project over the rotary screw 117. Then, the frame tube 103 is drawn out from the main body 108 and the inserting section 102 by drawing the screw 113 toward the operator. As a result, the solid state imaging device 45 including the objective lens system 106 can be removed from the inner tube 21 with accommodated in the frame tube 103.

The assembling operation is performed conversely.

The effect of this embodiment is the same as that obtainable from the first embodiment.

Figure 6:
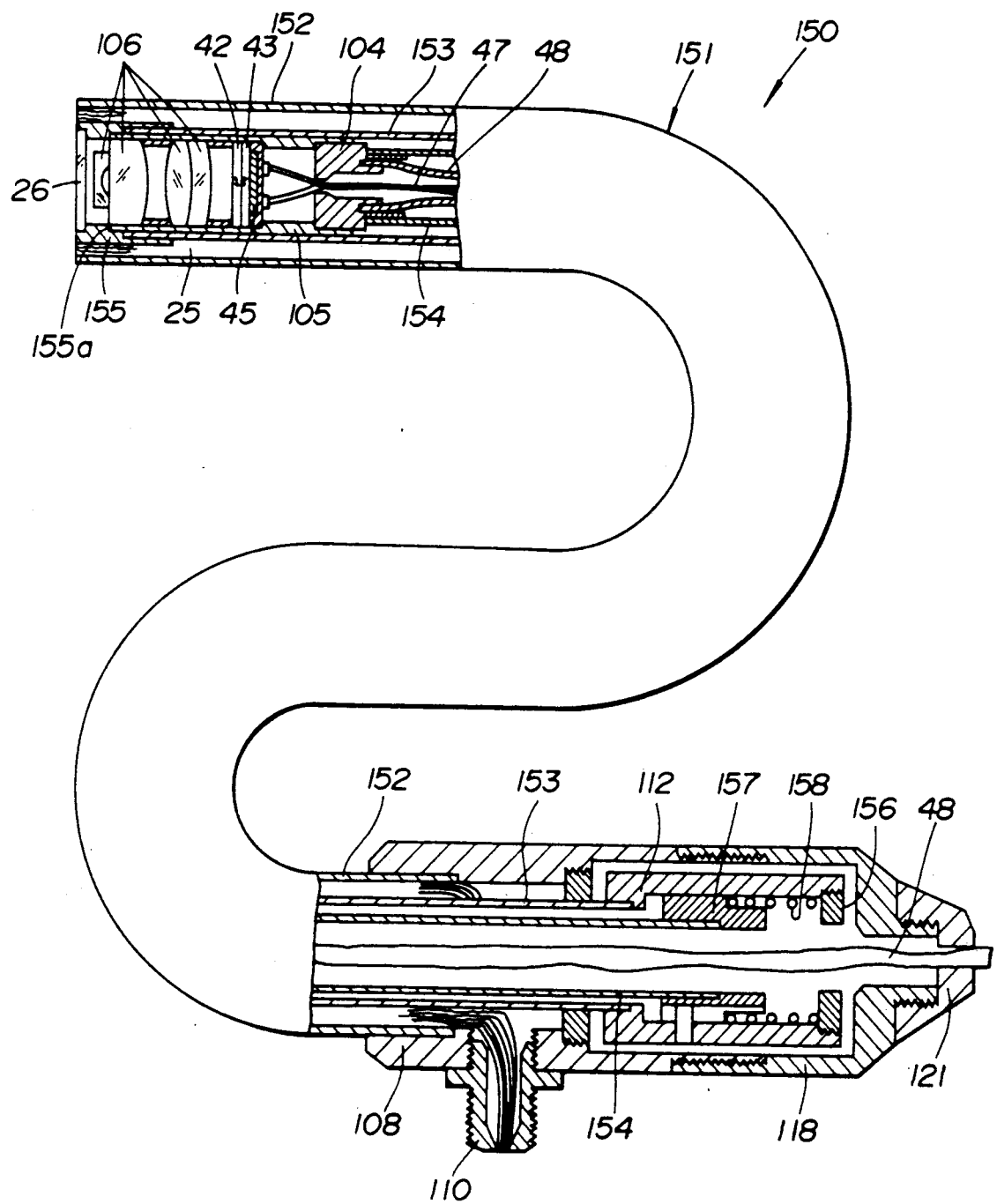
FIG. 6 is a cross sectional view which illustrates the electronic scope according to a fourth embodiment of the present invention.

FIG. 6 is a cross sectional view which illustrates a fourth embodiment of the electronic scope according to the present invention.

The difference of an electronic scope 150 according to this embodiment from that according to the third embodiment lies in that an inserting section 151 has a flexibility.

An outer tube 152, an inner tube 153 and a frame tube 154 serving as the frame member respectively comprise flexible tube each of which has a certain rigidity. Therefore, the above-described tubes 152, 153 and 154 can be warped as desired.

A cover glass frame 155 is fastened to the front portion of the inner tube 153, the cover glass frame 155 having a stepped portion 155a formed on the inner surface thereof so that the device frame 105 to which the objective lens system 106 and the solid imaging device 45 are fastened is fitted with the stepped portion 155a. As a result of the stepped portion 155a thus formed, the distance between the cover glass 26 and the objective lens system 106 can be maintained constant.

On the other hand, a nut 156 is screwed to the portion, which is adjacent to the operator, of the retaining member 112 and disposed in the portion, which is adjacent to the operator, of the inner tube 153 so that a spring 158 which urges a slider 157 disposed in the end portion, which is adjacent to the operator, of the frame tube 154 and capable of moving in the retaining member 112 is fixed.

The other structures are the same as those according to the third embodiment. A warp allowing mechanism may be provided for a vacant space.

Then, the operation of this embodiment will be described.

When the solid state imaging device 45 is interchanged, the cover 118 screwed in the portion, which is adjacent to the operator, of the main body is removed and the nut 156 is removed from the retaining member 112. Then, the frame tube 154 is drawn out from the inserting section 151 so that the solid state imaging device 45 in the device frame 105 is interchanged.

The assembling can be performed conversely to the removing operation.

According to this embodiment, since the inserting section 151 comprises a flexible tube (however, the frame tube 105 in the front portion of the frame tube 154 and the cover glass frame 24 in the front portion of the inner tube 153 are respectively made of rigid materials), the inserting section 151 can be warped. Furthermore, since the spring 158 always presses the frame tube 154 toward the cover glass 26, the distance between the cover glass 26 and the objective lens system 106 can be always maintained constant by the stepped portion 155a even if the positional relationship between the inner tube 153 and the frame tube 154 is deviated. As a result, an eclipse of the visual field or the like can be prevented.

The other effects are the same as those obtainable according to the first embodiment.

Figure 7:
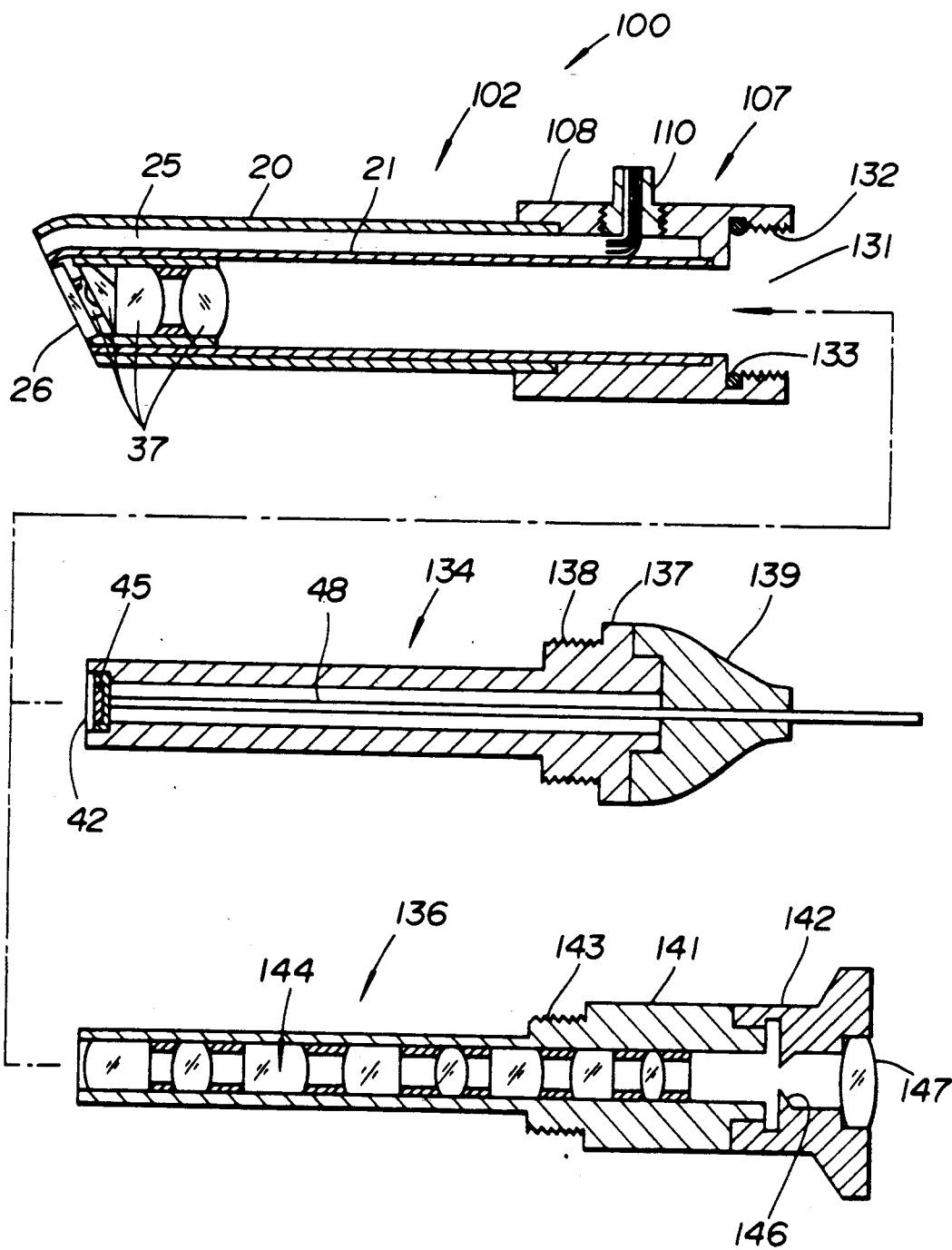
FIG. 7 is a cross sectional view which illustrates a fifth embodiment of the present invention of an electronic/optical scope in which the imaging system thereof and the image transmitting optical system thereof can be interchanged.

FIG. 7 is an exploded cross sectional view which illustrates a fifth embodiment of an electronic/optical scope according to the present invention.

The difference between an electronic/optical scope 100 according to this embodiment and the electronic scope according to the third embodiment lies in that a lens optical system may as well be used so that it can be used as an optical scope through which an image can be observed by the naked eye and which comprises an image guide including a relay lens system even if the solid state imaging device 45 encounters a failure.

Referring to FIG. 7, the inserting section 102 is arranged in such a manner that the inner tube 21 is inserted into the outer tube 20 and the light guide bundle 25 is disposed between the outer tube 20 and the inner tube 21. The glass cover 26 is disposed in the front portion of the inner tube 21 in such a manner that a plane which coincides with the light emitting surface of the light guide bundle 25 is formed. Furthermore, the objective lens system 37 is secured behind the glass cover 26.

The end portion, which is adjacent to the operator, of the outer tube 20 is directly connected to the main body 108 of the main body section 107, while the light guide bundle 25 disposed between the outer tube 20 and the inner tube 21 is introduced to the joint 110 which is allowed to project on the side surface of the main body 108.

The end portion, which is adjacent to the operator, of the inner tube 21 is connected to the central portion of the main body 108 so that the frame tube insertion port 131 formed in the rear end portion of the main body 108 is connected to the inner portion of the inner tube 21. The frame tube insertion port 131 has a female thread portion 132 to which an "0" ring 133 for hermetically sealing the joint portion is fastened in the base portion thereof.

A solid state imaging device frame tube 134 for constituting an imaging system or a relay lens system frame tube 136 for constituting an image transmitting system is arranged to be inserted into the inserting section 102 through the above-described frame tube insertion port 131.

The solid state imaging device frame tube 134 is arranged to be in the form of an elongated tube to which the solid state imaging device 45 is disposed in the front portion thereof. Furthermore, a joint portion 137 is formed in the end portion, which is adjacent to the operator, of the solid state imaging device frame tube 134. The infrared ray cutting filter 42, the quartz filter or the mosaic filter is disposed on the front surface of the solid state imaging device 45.

A male portion 138 which can be screwed into a female portion 132 of the main body 108 is formed in the outer surface of the joint portion 137. The signal line 47 connected to the solid state imaging device 45 and a holding member 139 for protecting the base portion of the shield 48 for covering the signal line are, from outside, secured to the end portion of the joint portion 137.

The signal line 47 is connected to a control circuit (omitted from illustration) so that a drive signal is transmitted to the solid state imaging device 45 and an electric signal read in response to the above-described drive signal is transmitted to the control circuit.

The relay lens system frame tube 136 is arranged to be in the form of an elongated tube. Furthermore, a large-diameter main body section 141 is formed in the end portion, which is adjacent to the operator, of the relay lens system frame tube 136. In addition, an eye-piece 142 is, from outside, secured to the end portion, which is adjacent to the operator, of the main body section 141. A male thread portion 143 which can be screwed into a female thread portion 132 of the main body 108 is formed on the outer surface of the main body 141. The relay lens system frame tube 136 accommodates a relay lens system 144 acting to transmit an image from the front portion thereof to the end portion, which is adjacent to the operator, of the main body section 141.

The above-described eye-piece 142 accommodates a mask 146 in the front portion thereof and an ocular lens 147 in its end portion adjacent to the operator in such a manner that the optical axis of the mask 146 and the ocular lens 147 coincide with that of the relay lens system 144.

The solid state imaging device frame tube 134 and the relay lens system frame tube 136 respectively shown in FIG. 7 are arranged so as to be screwed to the main body 108 of the inserting section 102. Therefore, if the solid state imaging device 45 cannot be used due to a failure or the like, the solid state imaging device frame tube 134 is removed. Furthermore, the relay lens system frame tube 136 is inserted so that the observation operation can be continued by the naked eye. Therefore, a scope which can be safely used can be realized.

On the contrary, if the relay lens system 144 cannot be used due to some reason, the solid state imaging device frame tube 134 can be used so as to continue the observation operation since it acts as an ordinary electronic scope.

As described above, according to the present invention, the solid state imaging device can be interchanged without a necessity of disassembling the elements constituting the inserting section. Therefore, the repairing or the interchanging work can be easily performed. Furthermore, the time in which the electronic scope cannot be used can be significantly shortened. In addition, the deterioration in the quality and the durability due to the repairing operation of the inserting section can be prevented, causing the safety to be improved.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

What is claimed is:

1. An electronic scope comprising:
   an elongated inserting section;
   a main body section to which the end portion of said inserting section is fastened;
   an objective lens system fastened to the front portion of said inserting section and arranged to form an optical image;
   a light guide allowed to pass through said inserting section and arranged to transmit illuminating light so as to emit it through the end portion thereof;
   a frame body the base portion of which is fastened to said main body section and the tail end portion of which is inserted into said inserting section until it reaches a position in the vicinity of the focal position of said objective lens;
   a solid state imaging device fastened to said tail end portion of said frame body, said solid state imaging device having a photoelectric transfer function; and
   securing means for detachably securing at least either said inserting section except for said frame body or said base portion of said frame body to said main body section.

2. An electronic scope according to claim 1, wherein said securing means is a screw-fastening means for securing said base portion of said inserting section into which said frame body is inserted to said main body section.

3. An electronic scope according to claim 1, wherein said inserting section is arranged in such a manner that the component of at least the outermost surface comprises a hard pipe member.

4. An electronic scope according to claim 1, wherein said inserting member is arranged in such a manner that the substantially overall portion of pipe members which constitute said inserting section is constituted by soft members.

5. An electronic scope according to claim 1, wherein the base portion of said light guide is fastened to said main body section and is arranged in such a manner that an end portion of a second light guide can be fastened so as to confront said base portion.

6. An electronic scope according to claim 1, wherein said frame body is eccentrically inserted into said inserting section.

7. An electronic scope according to claim 1, wherein said frame body is concentrically inserted into said inserting section.

8. An electronic scope according to claim 1, wherein said solid state imaging device is fastened to said frame body via a device frame fastened to the tail end portion of said frame body.

9. An electronic scope according to claim 1, wherein said objective lens system is a direct visual type arranged in such a manner that the direction in parallel to the axial direction of said inserting section is made to be the center of the imaging region.

10. An electronic scope according to claim 1, wherein said objective lens system is a perspective visual type arranged in such a manner that the direction which is not in parallel to the axial direction of said inserting section is made to be the center of the imaging region.

11. An electronic scope according to claim 1, wherein said light guide is allowed to extend from said main body section toward the side portion of said main body section.

12. An electronic scope according to claim 1, wherein a signal cable connected to said solid state imaging device is allowed to extend from said main body section to the side portion of said main body section.

13. An electronic scope according to claim 1, wherein said light guide is allowed to extend from said main body section toward the portion opposite to said inserting section.

14. An electronic scope according to claim 1, wherein a signal cable connected to said solid state imaging device is allowed to extend in a direction opposite to said inserting section.

15. An electronic scope according to claim 1, wherein said securing means has a function of preventing water invasion from a joint into the inside portion when said base portion of said frame body is fastened to said main body section.

16. An electronic scope according to claim 1, wherein said securing means is disposed at the rear end portion of said main body section so as to secure said frame body which is detachably inserted from the rear end portion of said main body section.

17. An electronic scope according to claim 1, wherein said frame body can be slidably inserted into a lens tube which is allowed to pass through an outer tube which constitutes said inserting section and having said objective lens system fastened to the tail end portion thereof.

18. An electronic scope according to claim 17, wherein said light guide is inserted between the inner surface of said outer tube and the outer surface of said lens tube.

19. An electronic scope according to claim 1, wherein said solid state imaging device is fastened to said frame body via a device frame fastened to the tail end portion of said frame body.

20. An electronic scope according to claim 19, wherein said solid state imaging device is secured to said device frame via detachable securing means.

21. An electronic scope according to claim 1, wherein drive means for moving said frame body in the axial direction of said inserting section is provided for said main body section.

22. An electronic scope according to claim 21, wherein said drive means has a focus adjustment function capable of adjusting the distance between said objective lens system and said solid state imaging device by moving said frame body.

23. An electronic scope according to claim 1, wherein said securing means is a screw-fastening means for securing said base portion of said frame body to said main body section.

24. An electronic scope according to claim 23, wherein the base portion of a second frame body to which a relay lens system through which an optical image can be transmitted can be fastened to said main body section in the case where said frame body is removed from said main body section.

25. An electronic scope according to claim 24, wherein an eye-piece to which an ocular lens is fastened is provided for the base portion of said second frame body.

* * * * *